United States Patent [19]

Weibezahn et al.

[11] Patent Number: 5,792,653
[45] Date of Patent: Aug. 11, 1998

[54] SUBSTRATE FOR CELL STRUCTURES

[75] Inventors: Karl Friedrich Weibezahn, Stutensee; Gudrun Knedlitschek, Karlsruhe; Hermann Dertinger, Heidelberg; Klaus Schubert, Karlsruhe; Thomas Schaller, Weingarten; Wilhelm Bier, Eggenstein-Leopoldshafen, all of Germany

[73] Assignee: Kernforschungszentrum Karlsruhe GmbH, Karlsruhe, Germany

[21] Appl. No.: 201,183

[22] Filed: Jan. 31, 1994

Related U.S. Application Data

[63] Continuation-in-part of PCT/DE92/00815 filed Sep. 23, 1992.

[30] Foreign Application Priority Data

Sep. 28, 1991 [DE] Germany ............ 41 32 379.3

[51] Int. Cl.$^6$ ............................................ C12M 3/00
[52] U.S. Cl. .................... 435/288.5; 435/283.1; 435/288.4; 435/288.7; 435/395; 435/401; 435/402
[58] Field of Search .................. 435/284, 285, 435/299, 300, 301, 286, 241, 297, 298, 240.241, 240.23, 240.243, 283.1, 288.4, 288.5, 288.7, 395, 401–402

[56] References Cited

U.S. PATENT DOCUMENTS

| | | | |
|---|---|---|---|
| 4,299,920 | 11/1981 | Peters | 435/288.4 |
| 5,108,704 | 4/1992 | Bowers et al. | 422/70 |
| 5,139,946 | 8/1992 | Howell et al. | 435/401 |
| 5,422,270 | 6/1995 | Caspi | 435/29 |
| 5,554,536 | 9/1996 | Rising | 435/305.1 |

FOREIGN PATENT DOCUMENTS

| | | |
|---|---|---|
| 0014007 | 8/1980 | European Pat. Off. . |
| 0170210 | 2/1986 | European Pat. Off. . |
| 0205790 | 12/1986 | European Pat. Off. . |
| 2522014 | 8/1983 | France . |
| 3938632 | 3/1991 | Germany . |

OTHER PUBLICATIONS

American Journal of Phynology vol. 251, No. 1, 1986, pp. C136–C139 R.E. Steele et al. "Porous–lotham dishes for cultive of polarized cells".

Primary Examiner—Leon B. Lankford, Jr.
Assistant Examiner—Christopher R. Tate
Attorney, Agent, or Firm—Klaus J. Bach

[57] ABSTRACT

In an apparatus for culturing cells which comprises a plate-like body with a lattice structure having openings separated from one another by sidewalls and a bottom disposed on one side of the lattice structure and having passages permeable for liquids but not for cells so as to form, with the lattice structure, cavities for receiving cells to be grown therein, the cavities have a clear width of between 50 μm and 1000 μm and the bottom consists of a material to which cells placed into the cavities will not easily attach so that the cells grow from the side walls of the cavities causing them to form a three-dimensional cell structure.

7 Claims, 6 Drawing Sheets

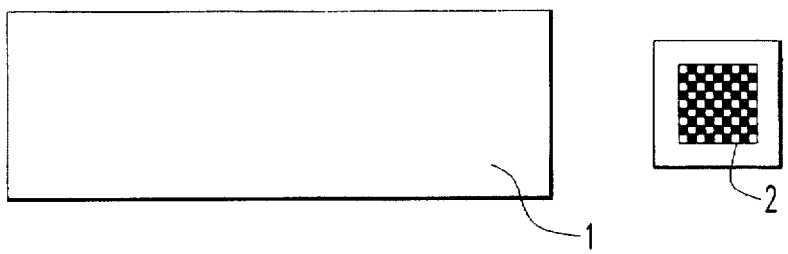
FIG.10a
FIG.10b
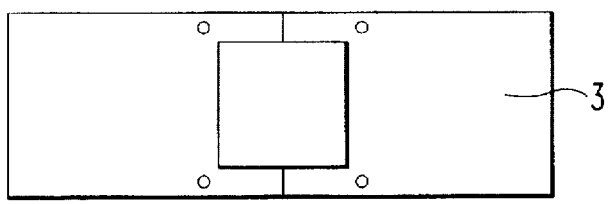
FIG.10c
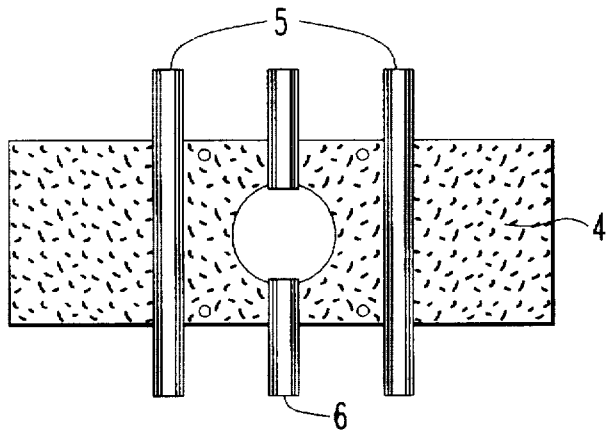
FIG.10d
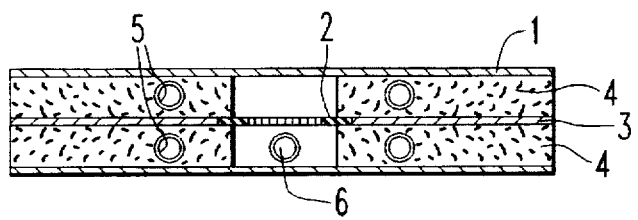
FIG.10e

SUBSTRATE FOR CELL STRUCTURES

The present application is a continuation-in-part application of international application PCT/DE92/00815 filed Sep. 23, 1992 and claiming the priority of German Patent Application P4132379.3 of Sep. 28, 1991.

BACKGROUND OF THE INVENTION

The invention relates to an apparatus for culturing cells comprising a lattice-like structure with cavities separated by walls and a bottom closing the cavities between the walls and being permeable for liquids but not for cells.

Such a substrate is known from DE 29 02 026 A1. The substrate disclosed therein comprises a lattice structure with a bottom which is removably connected to the lattice structure. The lattice structure consists of a plate of plastic material which includes a plurality of passages (chambers) separated from one another by webs. The chambers have a clear width of about 10 mm (10,000 μm).

The bottom may consist of a glass plate or preferably a plastic plate or plastic foil. With this substrate the cells develop on the bottom thereby generating essentially two-dimensional cell cultures. It is further pointed out that the bottom with the cell cultures thereon forms a microscopic object carrier or that it may be disposed on an object carrier of glass. This again assumes that the cells grow essentially only on the bottom and there, form an essentially two-dimensional layer.

From the publication "Morphological examinations with Fallopian tube epithelial tissue cells of the rabbit: Primary cultures of polycarbonate membranes" by I. G. Noske in TECNOMARA NEWS IV/90, Labortechnische Informationsschrift, a two-dimensional substrate for cell cultures and a two-dimensional cell culture are known. The substrate consists of a membrane with pores of different sizes. Some of these pores extend through the membrane. The cells have a tendency to anchor themselves in these pores. Essentially, the cells form a mono layer which covers the upper and lower surfaces of the membrane.

Such substrates have the advantage that a nutrient solution can easily be supplied to the cells and metabolic waste can easily be removed. Also, cells attached to such substrates can be observed optically under the microscope. It is however pointed out in this publication that the cells vary in shape depending on the kind of substrate utilized. They grow, for example, extremely flat on a glass or plastic bottom so that the polarity which is so important for their functions is not guaranteed.

In the article "Solid tissue masses formed in vitro from cells cultured on artificial capillaries" by Richard A. Knazek, Federation Proceedings, vol. 33, No. 8 (August 1974) and in a company brochure of the company "dunn Labortechnik GmbH" in Asbach, Germany, under the title "Cellmax™ 100-Hollow Fiber Bioreactor System for Mammalian and Insect Cell Culture" which refers to the Knazek publication, disclose a cell substrate which consists of a plurality of parallel capillaries arranged spaced from one another. The capillaries are combined at one end by a connecting member via which nutrient solution can be conducted through the capillaries. The cells grow on the outside of the capillaries in the spaces formed therebetween. The nutrient solution diffuses from inside the capillaries through the walls of the capillaries into the spaces therebetween for feeding the cells. In this manner, a three-dimensional cell structure is generated.

However, for different reasons, such a substrate is not very suitable for research with cell cultures. The metabolic gradient is not clearly defined because of the irregular geometry. Furthermore, the diffusion of compounds is always limited to certain molecular weights depending on the material used for the various capillaries. For some applications a coating of the substrate is necessary; such a coating may act as a diffusion barrier with this kind of cell substrate which would result in a collapse of the metabolic gradient. Finally, such a substrate cannot be arranged in such a manner that microscopic observation of the cells during cultivation is possible.

A further substrate for the cultivation of human and/or animal cells is disclosed in EP 0 205 790 B1. This substrate comprises a composite structure of pearl-like particles with a diameter of 50 to 300 μm with interstices in which three-dimensional cell cultures can develop. The pearl-like particles have on their surfaces macropores with diameters of less than 10 μm, preferably in the range of 0.1 to 3 μm. The macropores form a capillary system, into which the cells cannot grow since the diameter of the cells used herein is about 20 μm. However nutrients can be supplied through this system of capillaries and metabolic waste can be removed.

Nevertheless, such a substrate has essentially the same disadvantage as the capillary tube substrate.

FR-A2522014 discloses a plate-like substrate obtained by a molding process which has a plurality of cavities of a width of 10 to 1500 μm; it includes a bottom which is impermeable for liquids.

It is the object of the present invention to provide a cell substrate without the disadvantages mentioned above. Particularly, the advantages of membrane-like substrates are to be retained while the growth of three-dimensional cell structures is promoted.

SUMMARY OF THE INVENTION

In an apparatus for culturing cells which comprises a plate-like body with a lattice structure having openings separated from one another by sidewalls and a bottom disposed on one side of the lattice structure and having passages permeable for liquids but not for cells so as to form, with the lattice structure, cavities for receiving cells to be grown therein, the cavities have a clear width of between 50 μm and 1000 μm and the bottom consists of a material to which cells placed into the cavities will not easily attach so that the cells grow from the side walls of the cavities causing them to form a three-dimensional cell structure.

The openings in the lattice structure, in principle, may have any shape. Preferably, they are of rectangular or hexagonal shape because such structures can be formed with webs which have all the same length. With other, also for example, irregular shapes, the clear width should be in the given range in every direction. However, the clear width does not need to be constant. The openings may have, for example, the shape of oblong or hexagonal truncated pyramids such that they become narrower toward the bottom wherein the clear width as given should be maintained in any cross-sectional plane parallel to the bottom.

In spite of the fact that the substrate according to the invention has essentially the same shape as the one disclosed in DE 29 02 026 referred to above, the dimensions of the substrate according to the invention provide for essential differences in its effectiveness and in the way the cell cultures can grow on it. The dimensions of the substrate according to the invention are so selected that the cells disposed thereon do not (like in the known substrate described above) grow onto the bottom but anchor themselves to the side walls and produce a large number of interconnections in horizontal and particularly in vertical directions. In this manner, a compact three-dimensional cell structure is built up whose size is predetermined by the dimensions of the particular openings. As a result of the dimensions provided in accordance with the invention nutrition supply to the cell structures is also insured.

The basic idea in selecting the dimensions in accordance with the invention is to provide as little flat bottom surface as possible for the cells in developing the culture. It has been found that a three-dimensional build-up of the cell structure can no longer be obtained if several cells can attach themselves to the bottom surface and form a two-dimensional layer as in the substrate described above.

A substrate with cavities of a clear width in the range of 150 μm to 400 μm is preferred. Cavities with these dimensions are particularly suitable for cells with a diameter of 20 μm.

The depth of the cavities depends on the intended use of the substrate according to the invention. It is limited by the physiological requirement for a good nutrition supply for the central part of the cell structure in any Particular cavity. With this consideration in view, it appears that a depth of between 50 and 300 μm is most appropriate. However, for special nonphysiological applications, a depth in the range of 300 to 1000 μm appears to be more suitable. Such applications are, for example, experiments with tumor models wherein a central necrotic zone is intentionally generated.

Particularly preferred are substrates whose cavities have the shape of a truncated pyramid becoming smaller toward their bottom. Such substrates can be particularly easily produced by mechanical micromanufacturing procedures.

With a suitable selection of the width of the webs on the open lattice side, which is not covered by the bottom of the plate-like lattice structure, a well-defined cell structure layer can be produced on a very small area. In this arrangement the cells grow out of the cavities and join to form a cell structure which covers the whole substrate and which does not contain any objectionable support structure. To achieve this, it has been found that the width of the webs should be in the range of 15 to 115 μm.

With the substrate according to the invention the bottom is required actually only for the planting of the cell culture. Since, as a result of the dimensions provided in accordance with the invention, the cells anchor themselves to the walls of the cavities, it can be advantageous, particularly for microscopic examination of the cell culture, if the bottom is removable. This is possible since, in contrast to the prior art substrate referred to above, the cell culture is not connected to the bottom but to the walls of the cavities formed in the lattice structured plate-like substrate.

The bottom may comprise a microporous plate which is permeable only for liquids but not for any cells such as a ceramic frit provided with a respective plastic membrane. However, a lattice-like bottom plate with well-defined openings separated by walls is preferred. The sizes of the openings can be such that even single cells are prevented from passing therethrough.

In any case, the bottom is, in accordance with the invention, so designed that the cells placed into the cavities, essentially, cannot attach themselves to the bottom.

This can be achieved by a structure wherein the bottom does not have a flat area sufficiently large to accommodate a cell. If, for example, a ceramic frit is used as a bottom, the porosity of the frit should be selected accordingly. However, the bottom may also be a plate or foil which consists of a material that is not suitable for the attachment of cells.

The plates or foils used as bottoms for the cell substrates in the known arrangements have free surface areas between the pores whose widths are generally within a certain range. A more even-sized bottom can be made with a regular lattice structure with openings separated by walls. Such a lattice structure can also be made by the methods of micromanufacturing (mechanical micromanufacture, X-ray depth lithography or other lithographic procedures).

Particularly preferred are lattice-like bottom plates which, in principle, do not provide sufficient flat area for the cells placed thereon for attachment. To this end, the walls of the lattice structure utilized which are maximally 200 μm thick are in the range of 1 to 20 μm thick and the clear width of the openings, which is maximally 5 μm, is generally in the range of 1 to 5 μm. The lower limit of the dimensions of such a lattice structure will generally be limited by the manufacturing method. In the interest of unimpeded supply of nutrient solution and for appropriate removal of metabolic waste, the opening area in the bottom is larger than the bottom surface area occupied by the webs of the lattice structures.

It is advantageous if the substrate according to the invention consists of a transparent material. As a transparent material polymethylmethacrylate (PNMA) is particularly suitable. Substrates of PNNA can be easily made by micromanufacturing methods and PPMA has properties suitable for cell culture growth thereon.

Microscopic examinations are facilitated if the bottom plate can be removed from the lattice structure after establishment of the cell culture. If the substrate consists of a lattice structure plate with removable bottom it is sufficient if the lattice structure is made of a transparent material.

In some applications, the inner wall is of the cavities and the exposed surface areas of the bottom are coated in such a manner that the cells do not attach to the surfaces. In that case the substrate according to the invention is suitable not only for growing predetermined cell culture layers but also for the build-up of multicellular spheroids of a predetermined very uniform size. A coating suitable for this purpose is, for example, a silicon coating. With such a substrate, the cells deposited thereon aggregate in the various cavities. Then the clear width of the cavities determines the diameter of the spheroids grown therein.

The substrate according to the invention is, for example, a plate-like body which includes lattice-like structured square cavities disposed closely adjacent one another with a cross-section which becomes smaller with depth in the shape of an inversed truncated pyramid. At the bottom of the cavities there are substantially smaller openings in the shape of a truncated pyramid which openings extend through the bottom of the plate-like body. In this embodiment the plate-like body has an integral bottom which cannot be removed.

In another embodiment the substrate according to the invention comprises an open-ended lattice structure disposed on a microporous bottom plate, particularly a micro lattice bottom plate.

The three-dimensional cultivation of cells in the substrate according to the invention provides for cell differentiation in addition to the substrate contacts via cell-to-cell interactions. In addition to miroscopic observations series-slices of the substrate with the cells disposed therein can be prepared which is a distinctive advantage for the application of histological and histochemical methods.

The substrate according to the invention may be integrated into an object carrier or a medium circulation system.

With multilayer cell growth tight to the walls of the lattice structure, the substrate represents a kind of fabric filter with two physiological semispaces defined at opposite sides thereof. With different medium admission in the circulation system, vertically oriented metabolic gradients develop in the culture which are not blocked or inhibited by additional layer formation on the lattice structure (for example, with components of the extra cellular matrix with cell-specific applications).

The substrate according to the invention represents a rigid support structure for cells and facilitates the preparation of well-defined layers of various types of cells. As a result of the heterotypical cell interaction occurring in this connection processes cafferentiation processes can occur. It is, for example, possible to study cell-specific transport processes with such systems. Specifically, the functions of the organ system "skin" whose restitution in vitro is difficult, can be studied more closely by passing air through one of the semispaces as a medium.

Such a closely organ-like culture technique on the basis of the substrate according to the invention can be used with a large number of different types of cells. It can be utilized for the studying of phenomena in many biomedical areas wherein a high measure of cell differentiation is required:

toxicological examinations under near real conditions;

in the development of medications;

effectiveness and restitution testing;

in basic research;

as an alternative to animal experiments, particularly in connection with examinations of complicated organ systems (for example, the liver or the skin).

BRIEF DESCRIPTION OF THE DRAWINGS

FIGS. 3 to 5 show different steps for a mold insert with which an embodiment of the substrate according to the invention can be formed, specifically

FIG. 3b is a side view of the mold of FIG. 3a;

FIG. 4 shows the roughly structured mold insert;

FIG. 5 shows the finely structured mold insert;

FIGS. 10a–10e show a microscope objective carrier into which a substrate is integrated.

DESCRIPTION OF THE PREFERRED EMBODIMENTS—EXAMPLES

1. Making a substrate according to the invention

The substrate according to the invention can be made by X-ray lithographic procedures or by molding procedures.

Below a molding procedure is described on the basis of FIGS. 3 to 8 by which a plurality of the substrates according to the invention can be manufactured in series in a simple manner.

For the molding of a substrate of a resin material, a mold insert is required which is provided with positive structures for forming the cavities and openings of the microstructured substrate.

Figure 1:
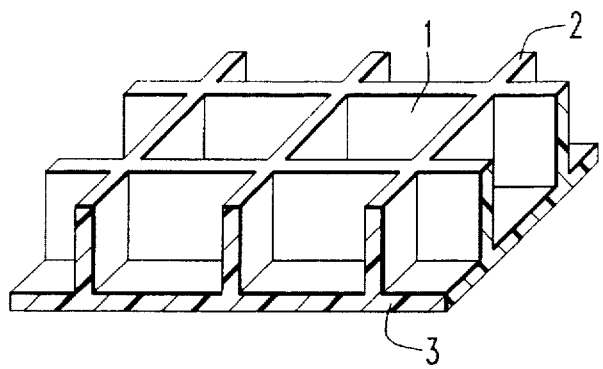
FIG. 1 shows an embodiment of the substrate with square openings and lattice webs 2 with a porous bottom plate 3.
Figure 2A:
FIG. 2a shows schematically the arrangement of FIG. 1.
Figure 2B:
FIG. 2b shows schematically an arrangement with webs of inverted V-shaped cross-section.
Figure 3A:
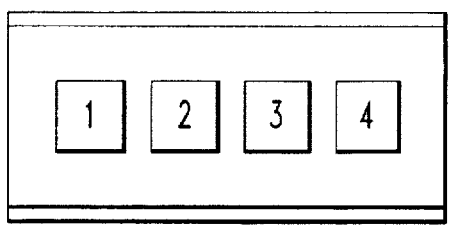
FIG. 3a shows the prepared mold insert.
Figure 3B:
Figure 4:
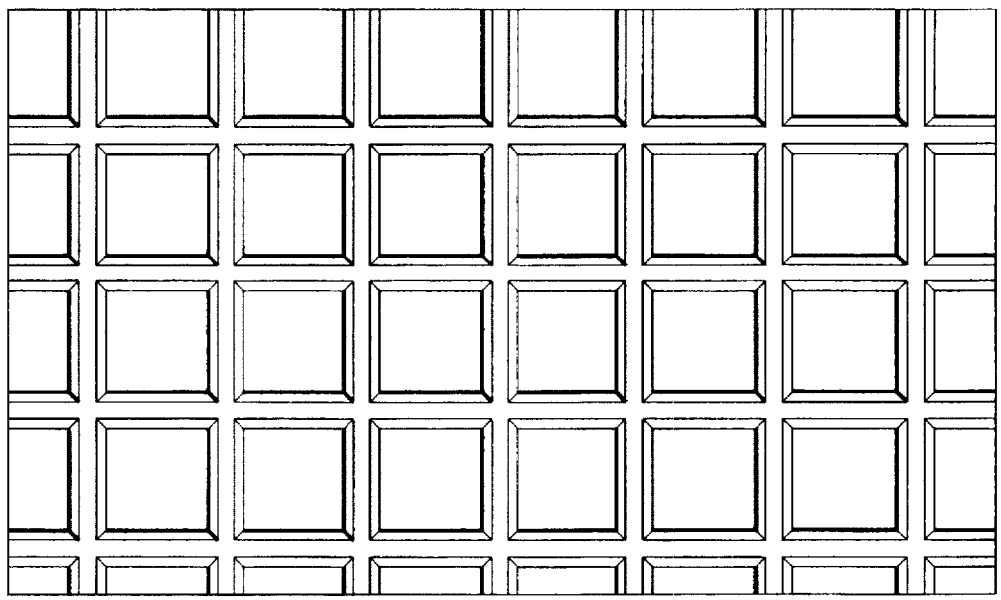

FIG. 3 shows a premachined mold insert with four raised areas 1 to 4 of 10×10 mm in size. The height of the raised areas is 1 mm. Wedge-shaped profiled diamonds are used to cut intersecting grooves into the top surface of the raised area in such a manner that a square raster of 400 µm square net structure of 280 µm deep grooves of triangular cross-section are formed such that frustopyramidal portions with top surface areas of 300 µm×300 µm remain between the grooves. This rough structured shape of the mold insert is shown in FIG. 4.

Figure 5:
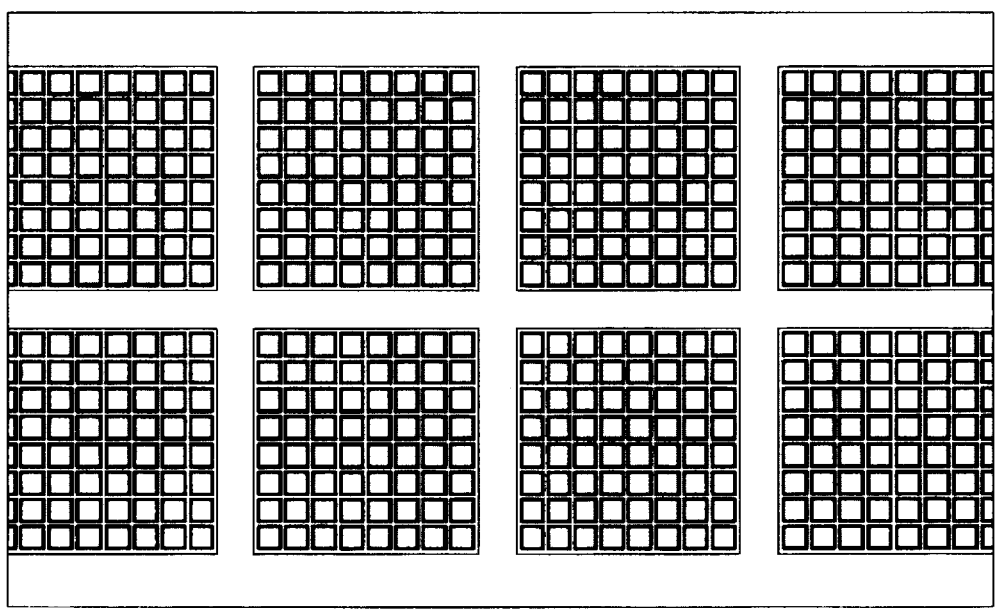

Subsequently, a substructure of intersecting small grooves is cut into the top surfaces of the frustopyramidal portion utilizing finer diamonds: The top surface of each frustopyramidal portion is provided with a square raster pattern of 40 µm with 8×8 microfrustopyramidal portions. The height of these microfrustopyramidal portions is about 80 µm; their top surfaces are about 10 µm$^2$. The result of this preparation step is shown in FIG. 5.

Figure 6:
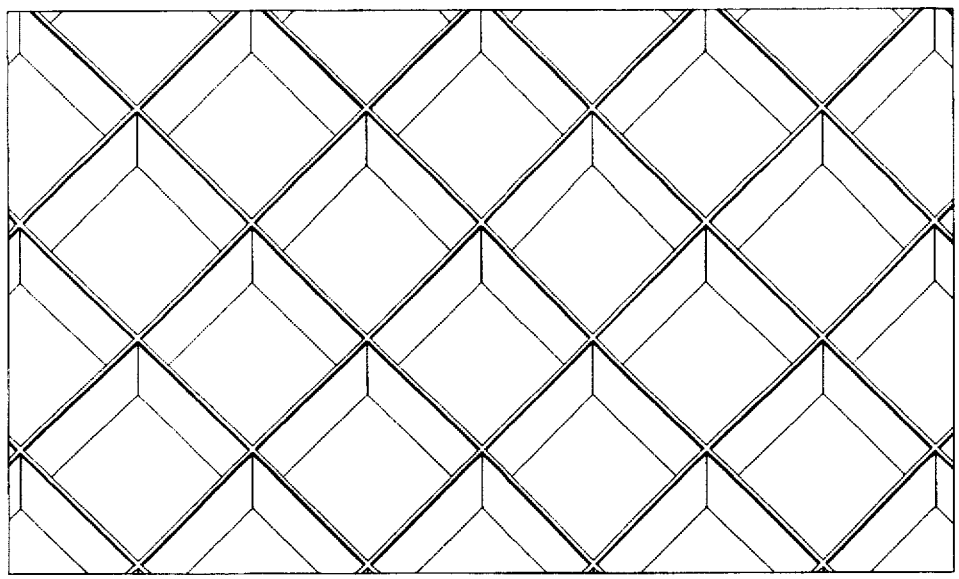
FIG. 6 shows a lattice obtained with the roughly structured mold.
Figure 7:
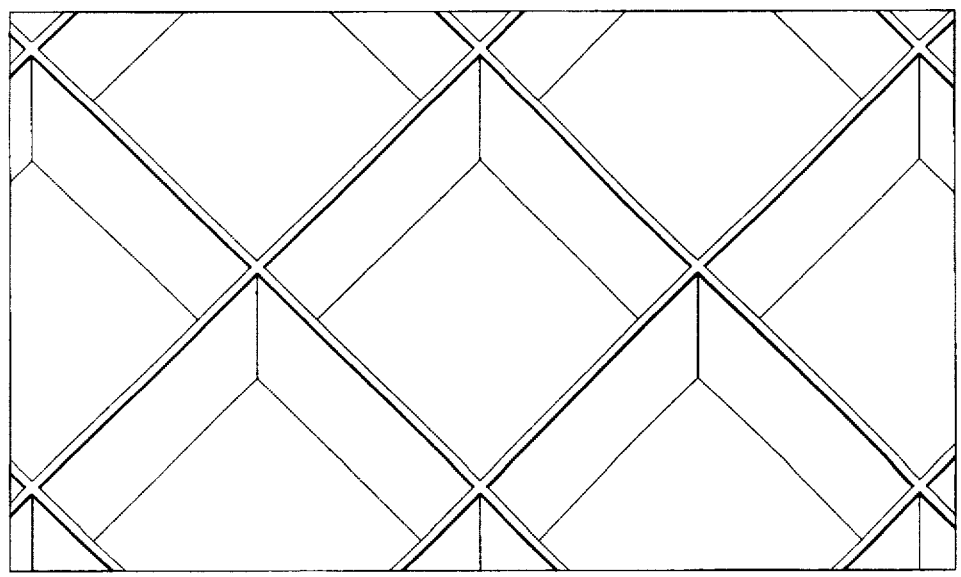
FIG. 7 shows a web structure molded with the finely structured mold insert with small depressions at the bottom of the cavities separated by the webs from which then the passages are formed.
Figure 8:
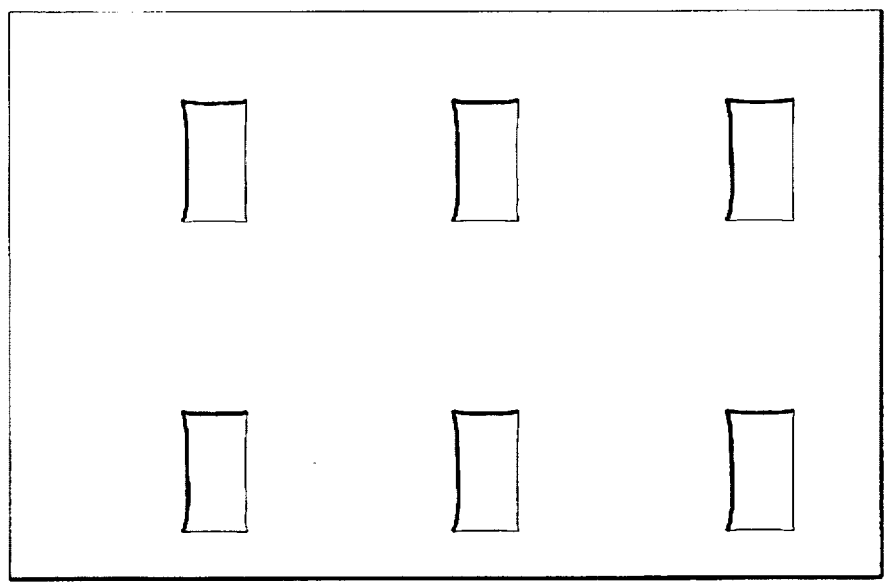
FIG. 8 shows the underside of the substrate from which a layer was cut off to form passages from the depressions.
Figure 9:
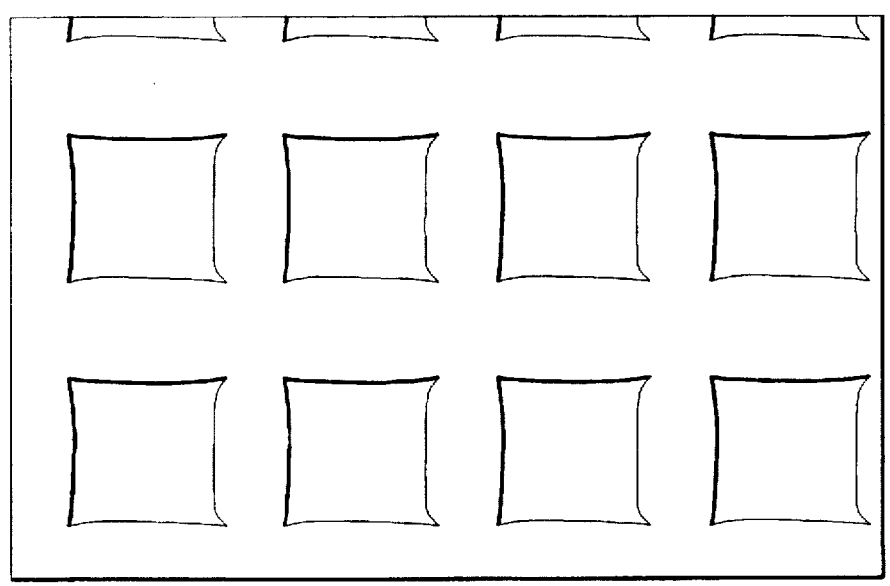
FIG. 9 is a top view of the substrate of FIG. 8.
Figure 11B:
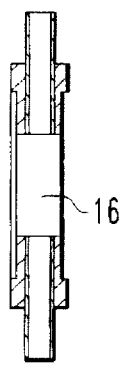
FIGS. 11a–11e show another microscope objective carrier with integrated substrate.
Figure 11A:
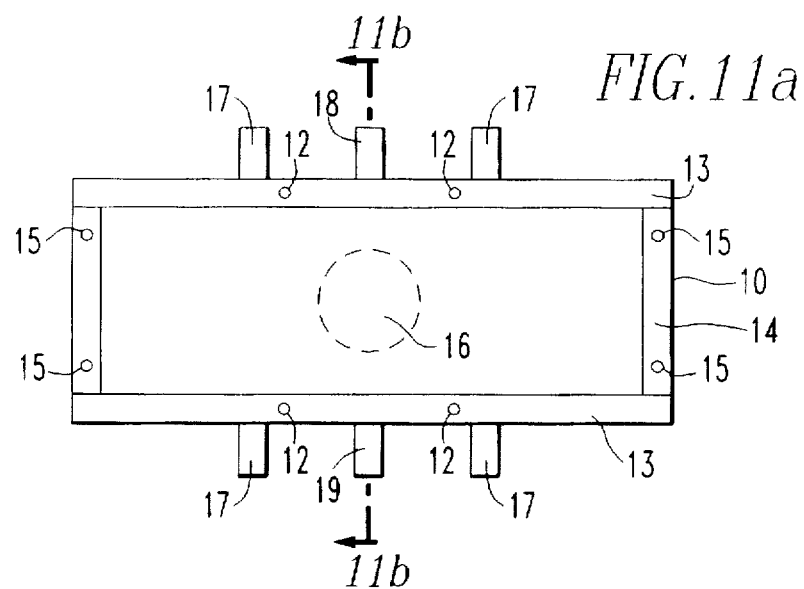
Figure 11C:
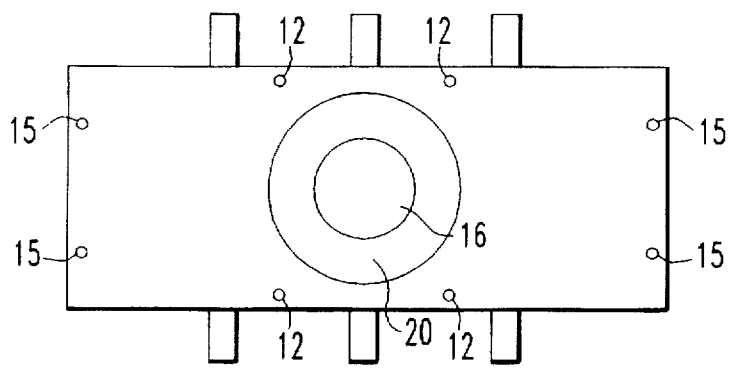
Figure 11D:
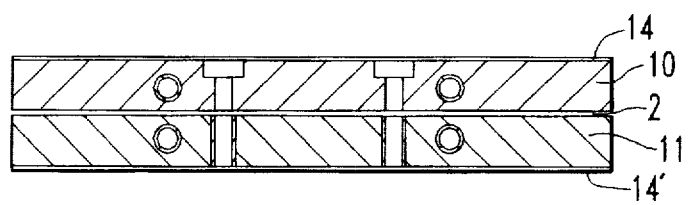
Figure 11E:
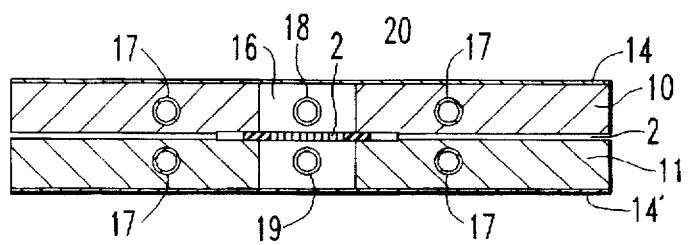

From the mold insert prepared in this manner a plate is formed in an injection molding machine. FIGS. 6 and 7 show the rough and the fine structure of the molded PNMA plate. In a final manufacturing step the material at the bottom of the molded substrate plate is removed; in this manner, the openings in the bottom of the substrate are exposed. For this step, the substrate is fixed on a vacuum mount and material is removed from the bottom side of the substrate until the openings or the pores are freed. The thickness of the bottom part can be controlled by the amount of material removed. Since the openings are conical their size, that is, their minimum diameter, can also be determined in this manner. The result of this process step is shown in FIG. 8 which shows the bottom side of the substrate and in FIG. 9 which shows the top side of the substrate. If the bottom of the substrate is totally removed, a resin lattice structure of 100 µm wide web portions and mesh apertures of 300 µm will be obtained which lattice structure may also serve as the plate-like lattice structured substrate.

2. Making a microscope object carrier

A substrate 2 made in the manner described under 1) and having a usable surface of 10 mm×10 mm is, as shown in FIG. 10, combined with two object carrier plates 1 of glass, an adjustment disc 3 and intermediate discs 4, which contain temperature control and nutrition channels 5 and 6 to form an object carrier.

The outermost channels 5 serve for the control of the temperature; nutrients are supplied and removed via the intermediate channels 6.

3. Manufacturing of another microscope object carrier

The microscope object carrier consists of two almost identical plates 10, 11 (FIGS. 11a–11d) between which a substrate 2 as manufactured under 1) is clamped so as to be liquid-sealed therebetween. The upper plate 10 and the lower plate 11 are identical except that four bores are provided near the edges of the upper plate and the lower plate has four threaded openings which are in alignment with the bores and into which screws extending through the bores are screwed for clamping the substrate between the plates. The Plates consist of brass and are finished by a galvanically deposited layer of rhodium for contact with the cell cultures. The outer surface is provided with an oblong recess of a width adapted to receive a commercially available microscope object carrier glass plate 14 which is retained by means of two plastic screws disposed at each short end of the plate 14 and received in passages 15. The plates are provided with a central opening 16 through which the cells in the substrate can be observed.

Inside, the plates are provided with a circular recess 20 adapted in size to receive the substrate 2.

Two tubes 17 with an inner diameter of 3 mm and an outer diameter of 4 mm extend through each plate for connection to a warm water source for maintaining a temperature suitable for cell activity. Center tubes 18, 19 extend from opposite sides into the center opening 16. They are used for conducting fresh nutrient to the space which is defined by the substrate 2 in the middle and outside by the respective glass plates 14, 14'. This arrangement when assembled provides for two spaces through which different nutrients can be conducted.

Accordingly, the system as a whole is built-up symmetrically from top to bottom by the following components:

Glass plate 14 screwed onto the upper plate 10 which is screwed to the lower plate 11 with the substrate 2 disposed therebetween to which another glass plate 14' is screwed.

With a substrate prepared in accordance with 1) the following biological experiments have been performed in order to demonstrate the growth of three-dimensional cell cultures.

4. Placing cells into the substrate

The experiments were performed with two permanent cell lines of the mouse: L- and SV40-3T3 cells. Throughout standard growth media were utilized.

First, the substrates were sterilized by $C_o$-gamma irradiation with about 100 Gy and were placed into a dry Petri dish. Then 300 but not more than 400 µl of a concentrated suspension of cells or spheroids (cell aggregates) were placed onto a 1 cm² large lattice structure of the substrate. Capillary action caused rapid penetration into the cavities of the substrate within about one minute carrying along the cells or spheroids. After about 15 minutes in an incubator at 37° C., the Petri dish was carefully filled with medium wherein two variations were tried out: In one experiment the medium was placed underneath the substrate such that the substrate was floating on the medium. In the other, the medium was deposited on top of the substrate. In both cases the cells in the substrate were fully contacted by the medium. Both methods proved to be equal with regard to further growth of the cells in the incubator. Supplying the nutrient medium to the substrate turned out to be without problems. Providing centrifugal forces for improving entrance of the cells or spheroids into the substrate was found unnecessary.

5. Cell affinity of the resin PMMA

A further objective of the experiment was the testing of the affinity of the cells regarding the substrate material. The formation of microscopically visible contacts with the substrate walls was taken as criterium. It appeared that the cells attached themselves to the walls of the cavities within a few hours. Together with vitality tests and further details of cell interaction with the cavity walls, the test demonstrates that the substrate material PMNA and the substrate geometry provide for good cell compatibility. The observed high affinity of the cells to the substrate material is possibly partially a result of the irradiation of the substrate for sterilization. The material surface alterations generated thereby (change of the charge pattern) may favor formation of cell contacts.

6. Vitality and growth behavior of the cells

The objective of the experiment, on one hand, was to identify any cell-damaging effects of the long-time cell growth in the substrate. On the other hand, the pattern of interaction of the cells with the cavity walls of the substrate and their morphologic differentiate on was to be tested. In order to identify any cell-damaging effects, cells and spheroids were cultivated in the substrate for more than 2 weeks. Nutrient supply was provided by an exchange of the medium every 2 to 3 days. During this period the culture remained sterile; the cells remained alive and capable of dividing. At the termination of the experiment all cells were still vital (as proved by a trypanoblue discrimination test) and capable of dividing (proved by a cloning capability test). Accordingly the system of culturing cells has no cell-damaging effects even over longer periods of time.

For producing and growing several layers of cells in the cavities of the substrate, single cells or cell spheroids can be utilized. In practice the selection is made depending on the properties of the types of cells used, for example, depending on their proliferation capability.

When single cells are placed into the cavities of a substrate they attach first to the walls of the cavities and generally in a selective manner about in the middle of a wall, that is, at half the height of the wall. Colonization of the porous bottom of a cavity is relatively rare. Starting at the walls the cells multiply without mechanical support toward the center of the cavity. A multilayer dense cell structure is formed. This behavior depends to a certain degree on the type of cell used and was particularly apparent with the use of L-fibroblasts.

For testing the behavior of spheroids, SV40-3T3 spheroids with an average diameter of 200 µm were placed into the cavities of a substrate. They were smaller than the cavities so that their growth behavior could be observed. They first attach themselves to a wall of the cavity. Cell growth then increases the volume of the spheroids so that, after a few days, the cavities are tightly filled. The formation of contacts of the outer cells of a spheroid with the walls of the substrate and accordingly the formation of a multilayer tissue-like cell structure could be observed microscopically as it occurred.

7. Removal of the cells for analysis. Reuse of the substrate

For further analysis the cells anchored in the cavities of a substrate can be dislodged by enzymatic treatment with Trypsin. A light-microscopic inspection shows that the cells are quantitatively removed from the cavities in this manner. A one-week long incubation of an emptied substrate showed that no cells had remained in the substrate cavities. This also demonstrated that the sterility was maintained. A substrate from which the cell culture was removed in this manner could be reused repeatedly.

What is claimed is:

1. An apparatus for culturing cells including a substrate to which said cells selectively attach, said substrate comprising:

a) a plate-like body with a lattice-like structure forming openings separated from one another by side walls, b) a bottom disposed on one side of said lattice-like structure, said bottom being formed by a micro lattice structure having webs with passages formed between the webs of said micro lattice structure, said webs being about 20 µm thick and the passages having a width of not more than 5 µm, said micro lattice structure being permeable for liquids but not for cells, and forming, with said lattice-like structure, cavities for receiving cells to be grown therein, c) said cavities having a width of between 50 µm and 1000 µm, and d) said bottom consisting of a material which prevents attachment thereto of cells placed into said cavities.

2. The apparatus according to claim 1, wherein the cavities in said lattice structure have a clear width of between 150 µm and 400 µm.

3. The apparatus according to claim 1, wherein the depth of said cavities for use of the substrate with physiological cell cultures is in the range of 50 µm to 300 µm.

4. The apparatus according to claim 1, wherein the depth of said cavities for use of the substrate with non-physiological cultures is between 300 µm and 1000 µm.

5. The apparatus according to claim 1, wherein, at the side of the lattice structure opposite said bottom, said side walls have a width in the range of 15 µm to 115 µm.

6. The apparatus according to claim 1, wherein the material of which said substrate is made is transparent.

7. The apparatus according to claim 6, wherein said substrate is mounted into a microscope object carrier.

* * * * *